United States Patent [19]
Pennig

[11] Patent Number: 5,827,282
[45] Date of Patent: *Oct. 27, 1998

[54] CLAMPING COUPLING

[75] Inventor: Dietmar Pennig, Cologne, Germany

[73] Assignee: Orthofix S.r.l., Italy

[ * ] Notice: The term of this patent shall not extend beyond the expiration date of Pat. No. 5,376,090.

[21] Appl. No.: 907,282

[22] Filed: Aug. 6, 1997

Related U.S. Application Data

[63] Continuation of Ser. No. 327,915, Oct. 24, 1995, abandoned, which is a continuation-in-part of Ser. No. 151,531, Nov. 12, 1993, Pat. No. 5,376,090, which is a continuation of Ser. No. 908,966, Jul. 6, 1992, abandoned.

[30]     Foreign Application Priority Data

Jul. 12, 1991 [DE] Germany ............. G 91 08 566.7

[51] Int. Cl.⁶ ............................................. A61F 5/04
[52] U.S. Cl. ........................... 606/54; 606/57; 606/59
[58] Field of Search ................... 606/53–59; 403/53, 403/59, 60

[56]         References Cited

U.S. PATENT DOCUMENTS

| | | | |
|---|---|---|---|
| Re. 31,809 | 1/1985 | Danieletto et al. | 606/57 |
| 4,135,505 | 1/1979 | Day | 606/59 |
| 4,714,076 | 12/1987 | Comte et al. | 606/57 |
| 4,848,368 | 7/1989 | Kronner | 606/57 |
| 5,019,077 | 5/1991 | De Bastiani et al. | 606/57 X |
| 5,152,280 | 10/1992 | Danieli | 606/57 |
| 5,342,360 | 8/1994 | Faccioli et al. | 606/59 |
| 5,376,090 | 12/1994 | Pennig | 606/59 X |
| 5,451,226 | 9/1995 | Pfeil et al. | 606/59 |

FOREIGN PATENT DOCUMENTS

| | | | |
|---|---|---|---|
| 420430 | 4/1991 | European Pat. Off. | 606/57 |
| 9007305 | 7/1990 | WIPO | 606/57 |

OTHER PUBLICATIONS

Orthofix, "Dynamic Axial Fixation".

*Primary Examiner*—Danton D. DeMille
*Attorney, Agent, or Firm*—Hopgood, Calimafde, Kalil & Judlowe

[57]         ABSTRACT

In application to an external fixator wherein at least one end of a fixator body is equipped with a first ball-joint component that is releasably connected or connectible to a second ball-joint component forming part of a bone-screw clamp, the invention provides a major capacity for enlarging the achievable range of possible angles as between the longitudinal axis of the bone-screw clamp and the longitudinal axis of the fixator body. Three different embodiments are disclosed. In a first disclosed embodiment, the expanded range is achieved by structural modification of the bone-screw clamp per se. In the other two embodiments, the expanded range is achieved by interposition of a connector unit having one of its respective ends a ball-joint connection component that is uniquely compatible with the ball-joint component of the fixator body and at the other of its ends a ball-joint connection component that is uniquely compatible with the ball-joint component of the bone-screw clamp.

5 Claims, 3 Drawing Sheets

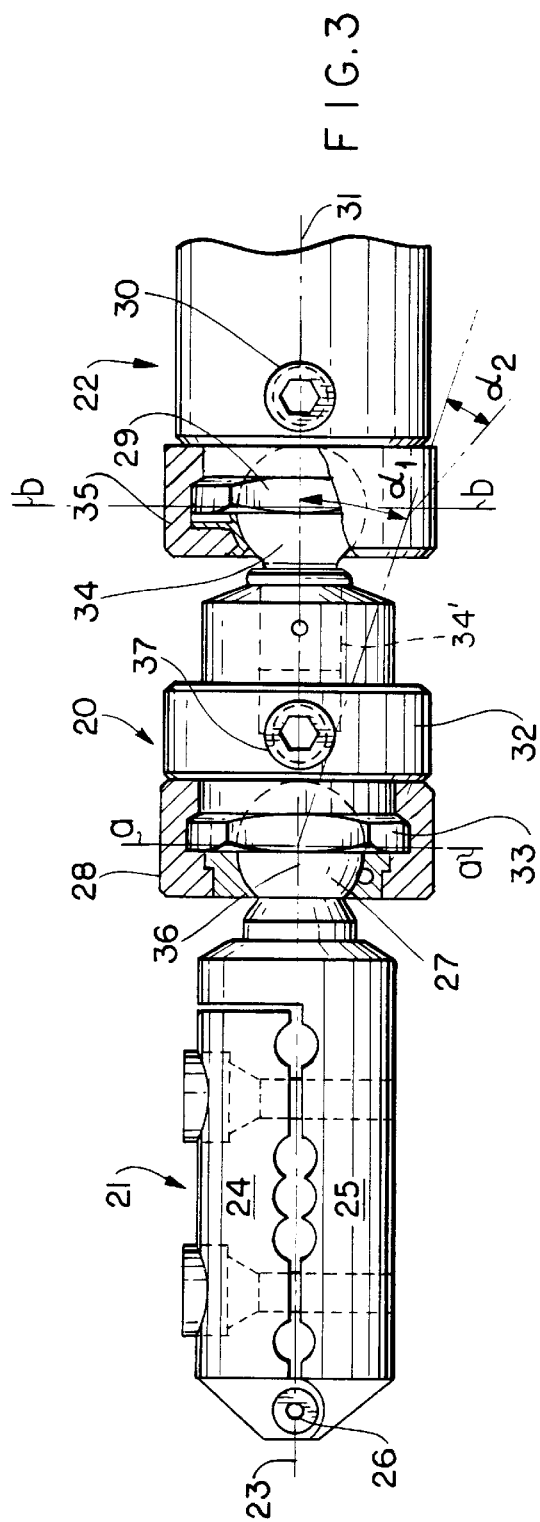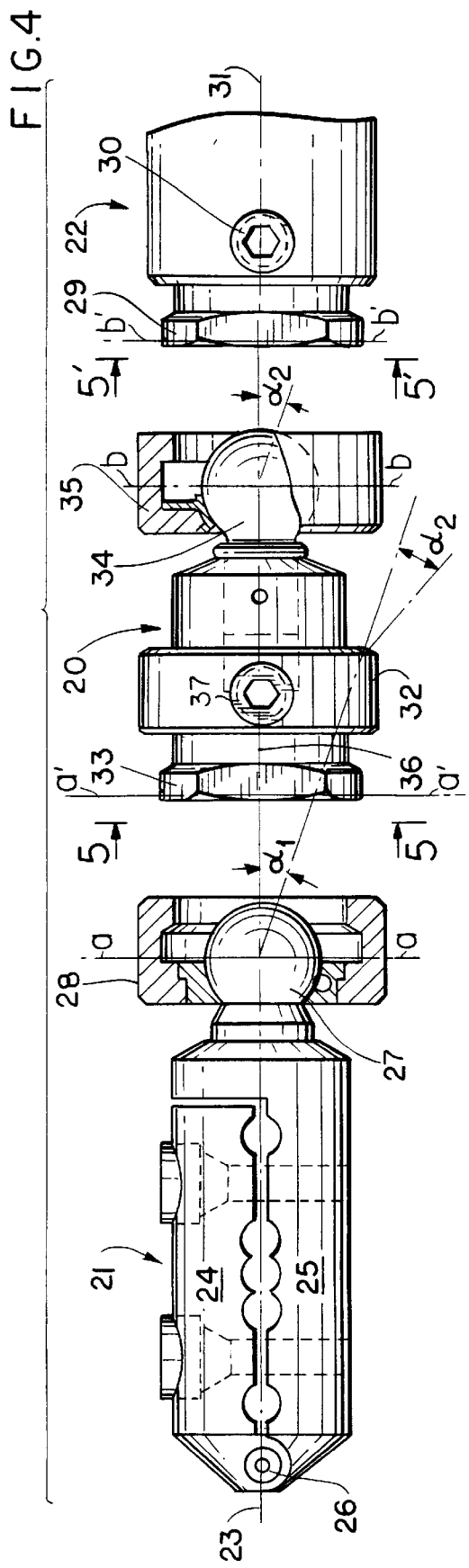

5,827,282

1

CLAMPING COUPLING

RELATED CASE

This application is a continuation of application Ser. No. 08/327,915 filed Oct. 24, 1994 now abandoned which is a Continuation-in-Part of co-pending application Ser. No. 08/151,531, filed Nov. 12, 1993 now U.S. Pat. No. 5,376,090 which is a continuation of original application Ser. No. 07/908,966, filed Jul. 6, 1992 now abandoned.

BACKGROUND OF THE INVENTION

The invention relates to orthopedic-fixator devices and in particular to a clamping coupling for a fixator of the nature disclosed in U.S. Pat. No. 4,312,339 (now Reissue Pat. No. Re. 31,809).

Said patent discloses an external fixator having a central body part with clamping means at each of the respective ends of the central body part. Each of the clamping means is developed (1) to receive and fix in place bone screws or pins and (2) to detachably achieve a ball-joint connection to the central body part, via a bayonet lock or a threaded lock. In this way, the bone screws are connected to the central body part of the fixator. The ball-joint connectors arranged at the ends can be angularly adjusted to an angle of about 40° to 45°, i.e., ±20° or more, with respect to the axis of the central part of the fixator, which angle is insufficient in certain cases.

SUMMARY OF THE INVENTION

The object of the present invention is to improve the indicated type of clamping coupling in such a way that, without great expense, larger angles can be achieved between the central body part of the fixator and the clamping coupling itself.

In one embodiment of the invention, this object is achieved by providing a clamping coupling wherein a rotary joint is interposed between the ball-joint connection of the fixator body and the clamping half shell which bears the ball-joint connection proper.

In a second embodiment, this object is achieved by providing an axially short interconnection unit, having a male ball-joint connection feature at one end and a female ball-joint connection feature at the opposite end. Thus, when interposed between (a) the ball-joint connection end of a bone-screw clamp and (b) the mating ball-joint connection end of a fixator body, there are two series-connected ball joints to provide essentially double the spherical range of angle adjustability that is available from a single ball joint.

In a third embodiment, the indicated object is achieved by providing an axially short interconnection unit, as in the second embodiment, but with a rotary joint between the male ball-joint connection feature at one end and the female ball-joint connection feature at the other end.

By these arrangements, a releasably clamped angling of 90° or more is now made possible as between the longitudinal axis of the bone-screw clamp and the longitudinal axis of the fixator body.

BRIEF DESCRIPTION OF THE DRAWINGS

The indicated three embodiments of the invention will be explained below with reference to the accompanying drawings, in which.

2

Figure 1:
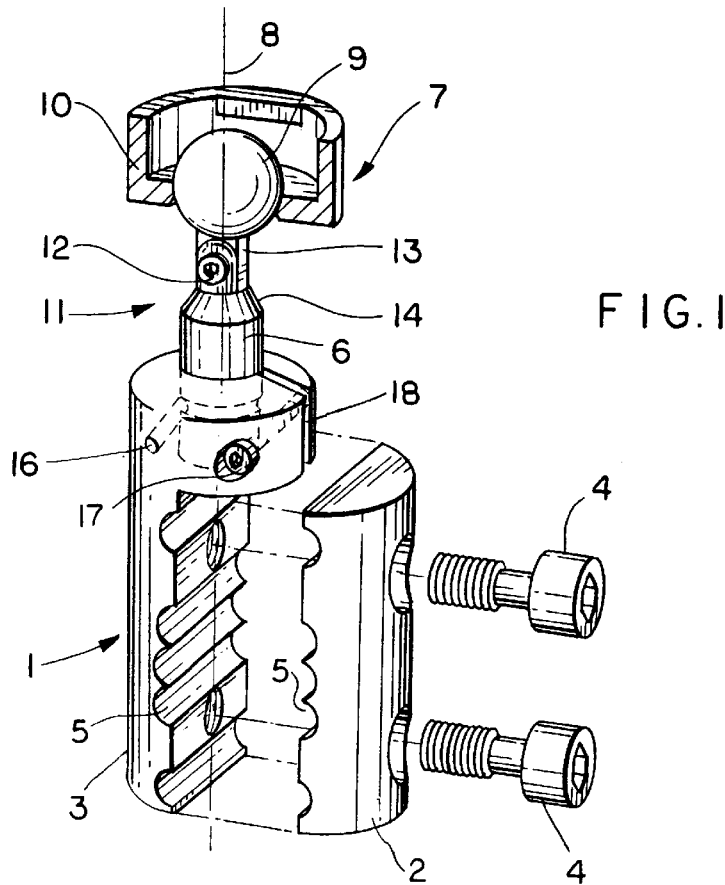
FIG. 1 an exploded view in perspective, partly in longitudinal section, showing a clamping coupling of the invention.
Figure 2:
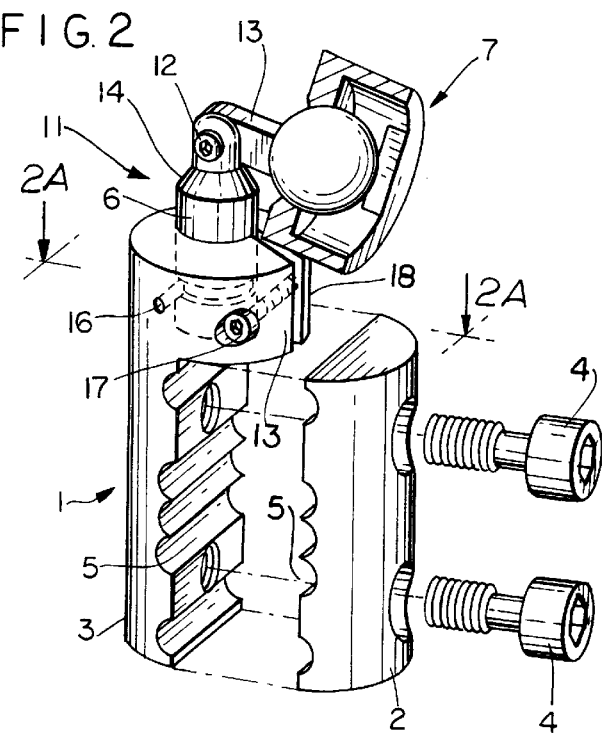
Figure 2A:
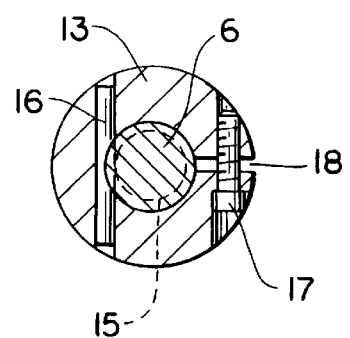
Figure 5:
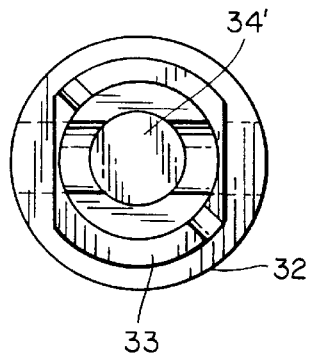
Figure 6:
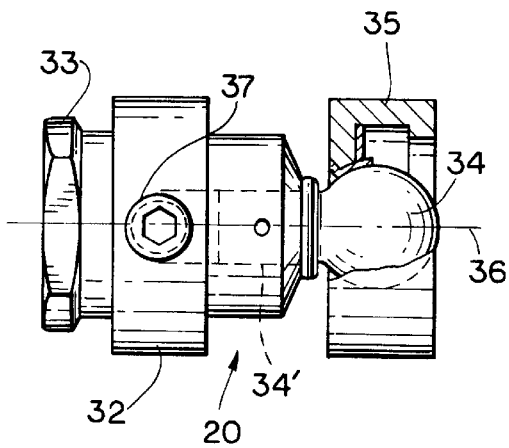
Figure 7:
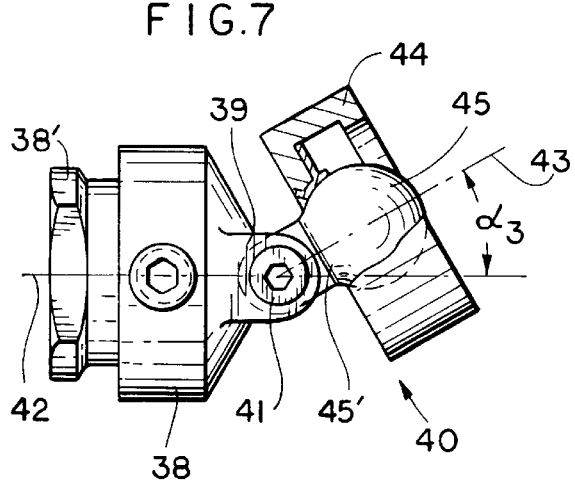
Figure 8:
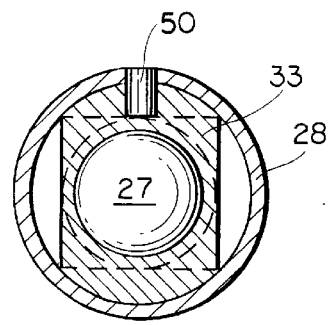

FIG. 2 is a similar view to illustrate enhanced angling through use of the coupling of FIG. 1;

FIG. 2A is a sectional view taken at 2A—2A of FIG. 2;

FIG. 3 is a view in side elevation of a second embodiment of the invention, in connected relation with one longitudinal end of a fixator body;

FIG. 4 is a view similar to FIG. 3, with detachably securable components in axially exploded relation;

FIG. 5 is an end view of male ball-joint connection features, viewable from each of the aspects 5—5 and 5'—5' of FIG. 4;

FIG. 6 is a side view in elevation of a unitary interconnection coupling which is central to the showings of FIGS. 4 and 5;

FIG. 7 is a side view in elevation of another unitary interconnection coupling embodiment;

FIG. 8 is a fragmentary section taken at a—a in FIG. 3; and

Figure 9:
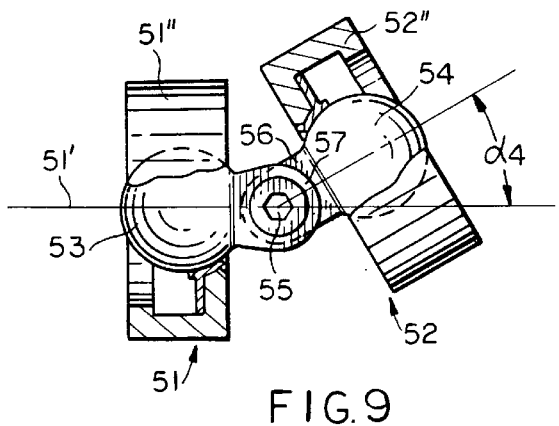

FIG. 9 is a view similar to FIG. 6, for a further coupling embodiment.

DETAILED DESCRIPTION

FIGS. 1 and 2 depict a clamping coupling 1 consisting essentially of two half shells 2 and 3, which can be fastened to each other by screws 4. Within the half shells 2 an 3 there are recesses 5 which will be understood to serve to receive and fix bone pins, screws or the like. The half shell 3 has an enlarged upper end which is adapted to provide releasably secured swivel action for a stem or shank portion 6 of a mount for a ball-joint connection 7. The swivel action is about the longitudinal axis 8 of the clamping coupling 1. The ball-joint connection 7 may be of screw-locking variety but is shown for bayonet-locking connection to an axial end of a known external fIxator (not shown). The ball-joint connection 7 consists of a ball 9 and a ring 10 which serves for detachable connection to the fixator.

For convenience of description herein, the ball-joint connection 7 will be termed a female ball-joint connection, in that its ring 10 is in retained relation to its associated ball 9, albeit loosely and rotatably retained, unless and until bayonet-engaged to a compatible male ball-joint connection at one of the ends of a fixator body.

In the prior art, the ball 9 of the ball-joint connection 7 directly and rigidly adjoins the half shell 3, but according to the invention, a rotary joint 11 is interposed between these two parts 3 and 7. The rotary joint 11 has a pivot pin 12, which will be understood to include threads by which the angle of the rotary joint 11 can be clamped or fixed, as by wrench application. The ball 9 adjoins the pivot pin 12 via a shank portion 13, and the half shell 3 adjoins pivot pin 12 via a clevis formation at a reduced end 14 of stem portion 6. By this arrangement, it is possible to swing the actual ball-joint connection 7, for example by 90° with respect to the axis 8 of clamping coupling 1, and to fix the ball-joint connection at a selected angular position, so that the range of use of the clamping coupling is thereby increased.

Further in accordance with the invention, a dimension of universality is added to the angular adjustment of rotary joint 11 by releasably clamped swivel action of stem 6, which is journaled for rotation about axis 8 in the enlarged upper end of half shell 3; an inserted pin 16 in this upper end of half shell 3 engages a circumferential groove 15 in stem 6, for axial retention of stem 6. Also, the enlarged upper end of half shell 3 is split at 18 to define jaws whereby a bolt 17 may be wrench-actuated for releasably clamped setting of a selected rotary position of stem 6 (and therefore also of the pivot axis of pin 12) about the longitudinal axis 8.

The second embodiment (FIGS. 3 to 6) is an interconnection unit 20, seen alone in FIG. 6, and seen in FIGS. 3 and 4 for its interconnecting relation between bone-screw clamping means 21 and one of the longitudinal ends of a fixator body 22; in FIG. 3, radial planes a—a and b—b include the center of ball connection at each of the respective ends of unit 20. The bone-screw clamping means 21 and the fixator body 22 may be of conventional, commercially available variety, as from Orthofix S.r.l. of Verona, Italy. In the case of current Orthofix products, the bone-screw clamp 21 comprises half shell elements 24, 25 having hinged articulation via their pivot-pin connection 26 at one end, and the ball 27 and ring 28 of a female ball-joint connection at the opposite end. The center of ball 27 is on the central longitudinal axis 23 of bone-screw clamp 21.

The fixator body 22 may be one of a variety of Orthofix devices having, at each of its respective longitudinal ends, a male ball-joint connection 29, that is compatible with the female connection means 28 (27) of the bone-screw clamp 21. A wrench-actuable eccentric pin 30 adjacent the male ball-joint connection 29 is journaled in the fixator body 22, for selective locking and release of compatible bayonet engagement with the female components 28 (27) of the bone-screw clamp 21, it being understood that, in the thus-engaged relation of clamp 21 to fixator body 22, the central longitudinal axis 31 of the fixator body would intersect the center of ball 27 of clamp 21, for any and all adjusted possible angular relationships between the respective longitudinal axes 23, 31 of clamp 21 and fixator body 22. As indicated above, this angle of conventional adjustability can be in the range ±20° or more.

In accordance with the invention, the interpositioning of unit 20 between an otherwise conventional bone-screw clamp 21 and the compatibly ball-joint connectible end of the fixator body 22, enables a doubling of the solid angle of releasably securable connection of the two otherwise conventional components 21, 22. To this end, the interconnection unit 20 provides at one end of its longitudinally short body 32, a male ball-joint connection element 33, which is preferably a duplicate of the male-connection element 29 of the fixator body; and at the opposite longitudinal end, unit 20 features female ball-joint connection elements comprising a ball 34 and a bayonet-locking ring 35, again preferably a duplicate of the compatible female connection elements 27, 28 of the bone-screw clamp 21. As shown, ball 34 is formed with a mounting stud 34', in pinned permanently fixed assembly to a local bore of body 32. In the interconnection unit 20, the respective male/female end connections are centered on a longitudinal axis 36, such that when in connected relation to clamp 21 and to fixator body 22, the axis 36 of unit 20 intersects with the axis 23 of clamp 21 at the center of ball 27, and the axis 36 of unit 20 also intersects with the fixator-body axis 31 at the center of ball 34. Stated in other words, in the exploded elevation of FIG. 4, the radial plane a'—a' includes the center of ball reception in the male connection component 33, and the radial plane b'—b' includes the center of ball reception in the male connection component 29. Upon bayonet assembly of unit 20 to unit 21, the ball-reception center in plane a'—a' merges with the ball center in plane a—a; and upon assembly of unit 20 to the fixator body end 22, the ball-reception canter in plane b'—b' merges with the ball center in plane b—b.

The body 32 of the interconnection unit 20 is further seen to include provision at 37 for wrench actuation of an eccentric pin, to determine releasably locked engagement of the male/female ball-joint socket 28/33 for ball 27, and of course wrench actuation of the eccentric pin 30 will similarly determine releasably locked engagement of the male/female ball-joint socket 29/35 for ball 34. Thus, an adjusted and clamped angle $\alpha_1$ of socket 28/33 connection to ball 27 can be effectively expanded by a further adjusted and clamped angular increment $\alpha_2$, to provide any desired total angle ($\alpha_1+\alpha_2$) between the bone-screw clamp axis 23 and the fixator body axis 31; and this total angle can be anything up to double the angular range of a conventional bayonet engagement, such as clamp 21 to fixator body 22 via the compatible male (29) and female (27/28) elements.

The embodiment of FIG. 7 is a modified interconnection unit 40, which incorporates a rotary joint, and unit 40 can be substituted for interconnection unit 20 in FIGS. 3 and 4, to obtain an even greater range of adjustably clamped angle between the bone-screw clamp axis 23 and the fixator body axis 31. This is made possible by the availability of a swivel connection via a pivot pin 41, between foldable halves 42, 43 of the body axis of unit 40, and by the incorporation of locking means for an adjusted angle of the pivot connection; the locking means for pivot 41 is not shown in FIG. 7 but will be understood to be similar to-that which is described for pivot 8 in FIGS. 1 and 2. More specifically, the left half of unit 40 is seen to comprise a body portion 38 with an integral male fitment 38' for selective engageability to female ball-joint connection means (as at 27/28), and at the other end of axis 42, a clevis formation 39 for pivot pin (41) connection to a flat stem integral part (45') of ball 45.

In FIG. 7, a pivot angle $\alpha_3$ is shown, and it will be understood that when unit 40 is connected and clamped to the bone-screw clamp 21 (by eccentric lock 46) and to the fixator-body end 22 (by eccentric lock 30), the maximum angle of adjusted relation between axes 23 and 31 can be the sum total of the adjusted angles $\alpha_1$, plus $\alpha_2$, plus $\alpha_3$. And even though pivot pin provides only a single transverse axis of articulation between its male connection end 42 and its female connection end at ring 44 and ball 45, the indicated maximum total angle is available throughout the same maximum solid angle, in view of the swivel nature of each ring 44 (28) about its associated ball 45 (27).

All three of the described embodiments will be seen to meet the stated object, and the range of solid angle adjustability and clamping is beyond that of copending application Ser. No. 08/151,531. The commercial article may be unitary as in FIGS. 1 and 2, and also unitary when interconnection unit (or 40) is locked in its assembly to a bone-screw clamp 21, as by a key pin 50 in ring 28 (FIG. 8), effectively locking the male/female bayonet engagement 28/23 against such partial relative rotation as would disengage the bayonet engagement. Also, the components 20, 21, 22 (or 21, 40, 22) in quantities of at least one of each component, may be commercial in kit form, preferably with two of the clamps 21 and two of the interconnection units 20 (40), for each fixator body 22 of the kit. Still further, the interconnection units 20 (40) may in themselves be separate articles of commerce, in view of their compatibility with existing bone-screw clamps 21 and fixator bodies 22.

FIG. 9 represents another kind of interconnection embodiment, wherein separate ball-joint connections of the same type, namely, female connections 51, 52, with their respective ball elements 53, 54, have releasably clamped hinged connection of their ball elements, at 55 and via stem and clevis formations 56, 57. Thus, integral formation of clevis 57 with ball 53 establishes a first central axis 51' of connection 51 and its ring 51", and the integral formation of a flat stem 56 with ball 54 establishes a second central axis 52' of connection 52 and its ring 52", with releasably clamped articulation of these axes about the pivot axis at 55. Provision of two female connections, with articulation about their respective axes, will be understood to enable connection of two standard fixator bodies to each other, with not only their selectively available angles of ball-joint connection to the adjacent male connection end of each of the fixator bodies, but these angles can also be augmented by the angle $\alpha_4$ to which the surgeon may choose to set the articulation of female connections 51, 52 to each other.

We claim:

1. As an article of manufacture, an elongate bone-screw clamping coupling having a longitudinal axis and having a rotary joint at one longitudinal end, the rotary joint having ball-joint connection means adapted for selective detachable connection to an external fixator, the ball joint connection means having a shank component extending therefrom, the rotary joint including the shank component and a longitudinal component part with a releasably clampable pivot means therebetween, the rotary joint being in close proximity to the ball-joint connection means so as to allow pivoting movement of the ball-joint connection means.

2. The article of claim 1, wherein the pivot means further comprises:

the shank component connected to the ball-joint means; and a clevis component connected to the clamping coupling.

3. The article of claim 2 wherein the pivot means further comprises:

a pivot pin operatively connecting the shank component and the clevis component.

4. The article of claim 1, in which the pivot means between the shank component and the longitudinal component part comprises a pivot pin operatively connecting said two parts.

5. A bone-screw clamping coupling having a first end, a second end, and a longitudinal axis, the coupling comprising:

ball-joint connection means, operatively connected to the first end of the clamping coupling, for selectively detachable connection to a lower portion of an external fixator; and a selectively clampable hinge, in close proximity to the ball-joint connection means and having an axis transverse to the longitudinal axis, the ball joint connection means having a shank component extending therefrom, the clampable hinge including the shank component and a longitudinal component part for connecting the ball-joint connection means to the first end of the clamping coupling in a selected clampable connection, the selected clampable connection providing for an adjustable rotary orientation of the hinge axis about the longitudinal axis wherein the hinge provides for the selective pivoting of the ball-joint connection means to the extent of about ninety degrees with respect to the longitudinal axis so that the range of use of the clamping coupling is increased.

* * * * *